(12) United States Patent
Ikramov et al.

(10) Patent No.: US 7,809,077 B2
(45) Date of Patent: Oct. 5, 2010

(54) METHOD FOR STABILISING TIME POSITION OF AN ULTRABANDWIDTH SIGNAL AND A LIVE OBJECT MONITORING LOCATOR FOR CARRYING OUT SAID METHOD

(75) Inventors: Gairat Saidkhakimovich Ikramov, ul. Pelshe, 16-108, Olimpiiskaya derevnya, Moscow (RU) 117602; Aleksandr Vladimirovich Andriyanov, Nizhny Novgorod (RU); Sergei Vasilevich Kuramshev, Nizhny Novgorod (RU)

(73) Assignees: Life Sensor Co., Ltd, Tokyo (JP); Gairat Saidkhakimovich Ikramov, Moscow (RU)

( * ) Notice: Subject to any disclaimer, the term of this patent is extended or adjusted under 35 U.S.C. 154(b) by 698 days.

(21) Appl. No.: 11/720,134

(22) PCT Filed: Sep. 26, 2005

(86) PCT No.: PCT/RU2005/000483

§ 371 (c)(1),
(2), (4) Date: May 24, 2007

(87) PCT Pub. No.: WO2006/038832

PCT Pub. Date: Apr. 13, 2006

(65) Prior Publication Data

US 2008/0220732 A1    Sep. 11, 2008

(30) Foreign Application Priority Data

Sep. 28, 2004 (RU) ............................... 2004128488

(51) Int. Cl.
*H04L 27/00* (2006.01)
*G06F 1/04* (2006.01)
*H03K 3/00* (2006.01)
*H03K 7/00* (2006.01)
*H03K 17/94* (2006.01)
*H03M 11/00* (2006.01)

(52) U.S. Cl. ........................ 375/295; 327/291; 332/106; 341/20

(58) Field of Classification Search ................. 375/295; 327/291; 332/106; 341/20
See application file for complete search history.

(56) References Cited

U.S. PATENT DOCUMENTS 6,497,656 B1 * 12/2002 Evans et al. .................. 600/300
6,822,604 B2 * 11/2004 Hall et al. ..................... 342/28

(Continued)

*Primary Examiner*—David C Payne
*Assistant Examiner*—Erin M File
(74) *Attorney, Agent, or Firm*—patenttm.us

(57) ABSTRACT

The invention relates to search and rescue service and can be used for debris active sounding. Said invention makes it possible to improve interference protection related to a temperature, the operator hands motion and trembling effecting the locator operation. The inventive method consists in forming an ultrabandwidth signal (UBW) according to a reference signal, in emitting the thus formed UBW signal to space, in receiving the UBW signal, in processing the UBW signal by correlating it with a reference UBW signal, wherein while processing the received UBW signal, the reference UBW signal is delayed for a time during which the initial position of a check point on a middle section between the maximum and minimum voltage of the correlated signal is set, in periodically monitoring the position of said check point and in modifying the space emission delay of the formed UBW signal when the check point position shifts from the initial position thereof, thereby resetting the check point position.

8 Claims, 7 Drawing Sheets

U.S. PATENT DOCUMENTS

| | | | |
|---|---|---|---|
| 7,129,886 B2 * | 10/2006 | Hall et al. | 342/28 |
| 7,345,618 B1 * | 3/2008 | Cole et al. | 342/22 |
| 7,508,860 B2 * | 3/2009 | Hyun et al. | 375/130 |
| 7,541,968 B2 * | 6/2009 | Hall et al. | 342/28 |
| 2002/0130807 A1 * | 9/2002 | Hall et al. | 342/28 |
| 2003/0058924 A1 * | 3/2003 | Darby et al. | 375/135 |
| 2004/0021599 A1 * | 2/2004 | Hall et al. | 342/28 |
| 2005/0083199 A1 * | 4/2005 | Hall et al. | 340/552 |
| 2006/0007988 A1 * | 1/2006 | Fullerton et al. | 375/130 |
| 2007/0153873 A1 * | 7/2007 | Fullerton | 375/130 |
| 2008/0111686 A1 * | 5/2008 | Hall et al. | 340/552 |

* cited by examiner

US 7,809,077 B2

METHOD FOR STABILISING TIME POSITION OF AN ULTRABANDWIDTH SIGNAL AND A LIVE OBJECT MONITORING LOCATOR FOR CARRYING OUT SAID METHOD

FIELD OF THE INVENTION

This invention relates to search and rescue service and may be used for active probing of debris caused by accidents and natural calamities for the purpose of objectively identifying possible presence of a human being exhibiting life signs, such as breath, heart beat, stir. It may be also used for medical purposes, e.g., remote measuring pulse and breath rate.

BACKGROUND OF THE INVENTION

Various devices are known in the art that use the action of radio-wave interferometer with the use of a compensation channel for separating the modulated component of a radio-frequency signal, which corresponds to the pulse or breath rate of a human being (RU, A, 2159942).

A microwave locator is known that comprises a modulator and a transmitter consisting of a generator, a power divider, a transmitting antenna, which are connected by their signal inputs to their signal outputs in series, and a receiver made with the possibility of emitting a radio-frequency modulated signal, which consists of a receiving antenna, a VHF receiver, a preamplifier/demodulator, a signal processing unit, which are connected by their signal outputs to their signal inputs in series, and made with the possibility of receiving a reflected radio-frequency signal modulated by the pulse and/or breath component from a living being and separating this component at the output of the preamplifier/demodulator, wherein the second signal output of the power divider is connected to the control input of the VHF receiver, the first control output of the modulator is connected to a transmitter and the second and the third outputs of the modulator are connected to the first and the second control inputs of the preamplifier/demodulator. (U.S. Pat. No. 4,958,638).

A disadvantage of the above technical solutions is their poor interference protection relating to various destabilizing factors influencing the locator operation, such as temperature, instability of locator position due to operator hands motion or trembling, instability of the position (movement) of a living being.

Equipment using ultra-wideband (UWB) signals started becoming common in 1960s after Tektronics and Hewlett-Packard issued stroboscopic oscilloscopes for measuring signal parameters. Stroboscopic oscilloscopes used the property of probing signal regular repetition for series restoration of its form. In combination with a source of an ultra-wideband signal (usually change of voltage with the front of picosecond duration was used) the stroboscopic oscilloscope was named a time-domain reflectometer.

The time-domain reflectometry method (TDR) become widespread not only for studying wave impedance, irregularities of distributed paths, but also for assessing dielectrics properties, determining soil humidity, measurements in semiconductor devices. This method gradually transformed into a wider line of time-domain measurements, where frequency characteristics of objects were obtained through the use of signal digital processing algorithms, e.g., fast Fourier transformation (FFT), which were similar to those measured by circuit frequency analyzers.

Ultra-wideband (UWB) signals are understood as signals for which a proportional frequency band $\Delta f = 2(F_H - F_L)/(F_H + F_L)$, where $F_H$ is the upper frequency in the signal spectrum, and $F_L$ is a low frequency in the area more than 0.25. This definition is not a single one; in some works the term "ultra-wideband signal" provides for a definite physical bandwidth (as a rule not less than 500 MHz), in other cases it is considered that such a bandwidth is located near zero frequency. Therefore such definitions are mostly conditional. But recently this term is of wide use, since radiotechnical processing methods for UWB signals have certain commonality and have been significantly developed. The term is applicable to various systems using electromagnetic signals of nanosecond and picosecond duration, systems of time-domain communication and measurements, time-domain reflectometers, radars with radio pulses with duration of several nanoseconds and less.

Works on creation of nanosecond pulse devices have been described in books, e.g., L. A. Morugin, G. V. Glebovich "Nanosecond Pulse Equipment", Sov. Radio, 1964; and Yu. A. Ryabinin "Stroboscopic Oscillography", M., Sov. Radio, 1973. A review of works on findings in the application of picosecond equipment may be found in the book by G. V. Glebovich, A. V. Andriyanov et al. "Object Studies with the Use of Picosecond Pulses".

Radio I Svyaz, 1984.

The use of UWB signals in the field of location has the same limitations as in VHF locators. Such limitations mainly relate to slow temperature drifts of signal time positions and to short-time changes in the position of a locator or an object under probing. But when using radio signals for stabilizing their time position (phase and frequency) phase locking is widely used, which is very difficult for use in the field of UWB signals when working with pulses of small duration. Nevertheless, stabilization of UWB signal positions is necessary and very important, since a delay of a signal received from a probed object varies with changes in temperature or the locator position. In order to read a signal from a given distance long-term stability of the UWB signal time positions is necessary. But in any electronic circuits the life period of any carriers depends on temperature, and time delay of signals may vary by a value up to 200-500 picoseconds. When using a probing signal with duration less than 1 nanosecond, this does not lead to a change in a delay of received signal amplitude from its maximum to zero value.

Until now no methods of stabilizing time positions of UWB signals are known.

The closest technical solution for the claimed one is an ultra-wideband radar for monitoring people, a patent for which has been granted to McEwan (U.S. Pat. No. 5,361,070).

This radar comprises a driving generator, a randomizer, units of reference delay and adjustable delay, two antennas, a generator of ultra-wideband (UWB) signals, a detector of received signals. For finding and monitoring people the transmitting antenna emits a UWB pulsed signal, and the receiving antenna receives a signal reflected from a human being. A reference delay and an adjustable delay serve only for separating a certain area according to a distance at which a reflected signal is registered.

This known technical solution has limited possibilities of monitoring living people due to the fact that the radar does not provide for searching for people at any distance, and when measuring parameters of a reflected signal the device is subject to influence of destabilizing factors, such as temperature and instability of the positions of both an identified object and the radar itself. When the said factors change, delays of registered signals and, consequently, amplitudes of registered voltages are varied accordingly. Due to the said factors the known radar may serve only as a locator of living beings at a predetermined distance.

SUMMARY OF THE INVENTION

The objective of this invention is to create a method for stabilizing time position of ultra-wideband signal and a locator, which would enable increasing long-term stability of time position of ultra-wideband signals and independence of their time position from temperature drifts or instability of emitting site and location of a probed object, which may be caused, e.g., by trembling of a transmitting device or shifting the position of a living being, as well as raise accuracy of ranging a living being and, thus, improve quality of UWB signal processing.

The stated objective is achieved by that the inventive method includes shaping an ultra-wideband signal according to a reference signal, emitting a formed ultra-wideband signal to space, receiving an ultra-wideband signal, processing a received ultra-wideband signal by correlating it with the reference ultra-wideband signal, wherein, while processing a received ultra-wideband signal, the reference ultra-wideband signal is delayed by a time during which an initial position of a check point in a middle range between the maximum and minimum voltages of the correlated signal is set, regularly monitoring a position of this check point, and if the position of the check point shifts as compared to the initial one a delay in emitting to space the formed ultra-wideband signal is changed thus resetting the check point position.

Other embodiments of carrying out the inventive method are possible, wherein it is expedient that:
  before receiving next ultra-wideband signals reflected from an object an initial position of a check point is set by emitting a formed ultra-wideband signal directly into a space area wherefrom next ultra-wideband signals reflected from an object are received;
  an initial position of a check point is set when receiving an ultra-wideband signal reflected from an immovable object;
  as the position of a check point its position in the range of the correlated signal having the maximum steepness is taken, at this the Uco value of reference correlated voltage is measured at that point, and if current Uc values of correlated voltage become different from the Uco value of the reference correlated voltage, a delay in emitting to space of a formed ultra-wideband signal is changed so as to take into account the current Uc value of correlated voltage, at negative steepness of a correlated signal at the check point and if Uc>Uco a delay being decreased, and if Uc<Uco, a delay is increased, or, at positive steepness of a correlated signal at the check point and if Uc>Uco, a delay being increased, and if Uc<Uco a delay is decreased;
  the stabilization parameter e is set, which is selected proceeding from the condition of Uco voltage exceeding a Un noise level at the check point;
  a pulse packet is used as an ultra-wideband signal, where the form of each pulse corresponds to one period of a harmonic vibration;
  a pulse packet of pseudo-random sequence is used as an ultra-wideband signal.

In order to achieve the stated objective a locator for monitoring living beings comprises a clock pulse generator, a pseudorandom sequence pulse generator, the first adjustable delay unit, the first ultra-wideband signal pulse shaper made controllable, a transmitting antenna, which are connected in series, the second adjustable delay unit, the second ultra-wideband signal pulse shaper, a mixer, an amplifier, a receiving antenna, the input of the said second adjustable delay unit being connected to the output of the said pseudorandom sequence pulse generator and the output of the said delay being connected to the input of the said second ultra-wideband signal pulse shaper which output being connected to the first input of the said mixer, the said receiving antenna being connected to the input of the said amplifier which output being connected to the second input of the said mixer, an adjustable amplifier, a band-pass filter, an analogue-to-digital converter, which are connected in series, the input of the said adjustable amplifier being connected to the output of the said mixer, a processing unit and a capacitor, one output of the said capacitor being connected to the output of the said mixer and the other output being connected to the housing, the clock input of the said processing unit being connected to the output of the said clock pulse generator and its control input being connected to the output of the said analogue-to-digital converter, the processing unit is made with five control outputs, the first control output of the processing unit is connected to the control input of the first ultra-wideband signal pulse shaper, its second control output is connected to the control input of the first adjustable delay unit, its third control output is connected to the control input of the second adjustable delay unit, its fourth control output is connected to the control input of the adjustable amplifier, and its fifth control output is connected to the control input of the pseudorandom sequence pulse generator, the processing unit is made with the possibility of selecting a modulated component corresponding to the pulse or breath rate of a living being, the said processing unit being made so as to ensure shaping of ultra-wideband signal pulse packets with the possibility of regularly switching on/off according to the control input of the first ultra-wideband signal pulse generator, the said processing unit being made so as to ensure changing a delay according to the control input of the second adjustable delay unit for the purpose of fixing a check point position at a middle range between the maximum and minimum voltages of a correlated signal at the capacitor, the said processing unit being made with the possibility of memorizing that check point position and changing a delay according to the control input of the first adjustable delay unit when that check point position is changed, the said processing unit being made so as to ensure changing a delay according to the control input of the second adjustable delay unit for the purpose of ranging a living being, and the said processing unit being made so as to ensure changing a gain coefficient of the adjustable amplifier for the purpose of compensating for attenuation of an ultra-wideband signal received by the receiving antenna if a distance to a living being is increased.

The above advantages as well as specific features of this invention will be better understood in the description of its preferred embodiments with references to the appended drawings.

DESCRIPTION OF PREFERRED EMBODIMENTS

Figure 1:
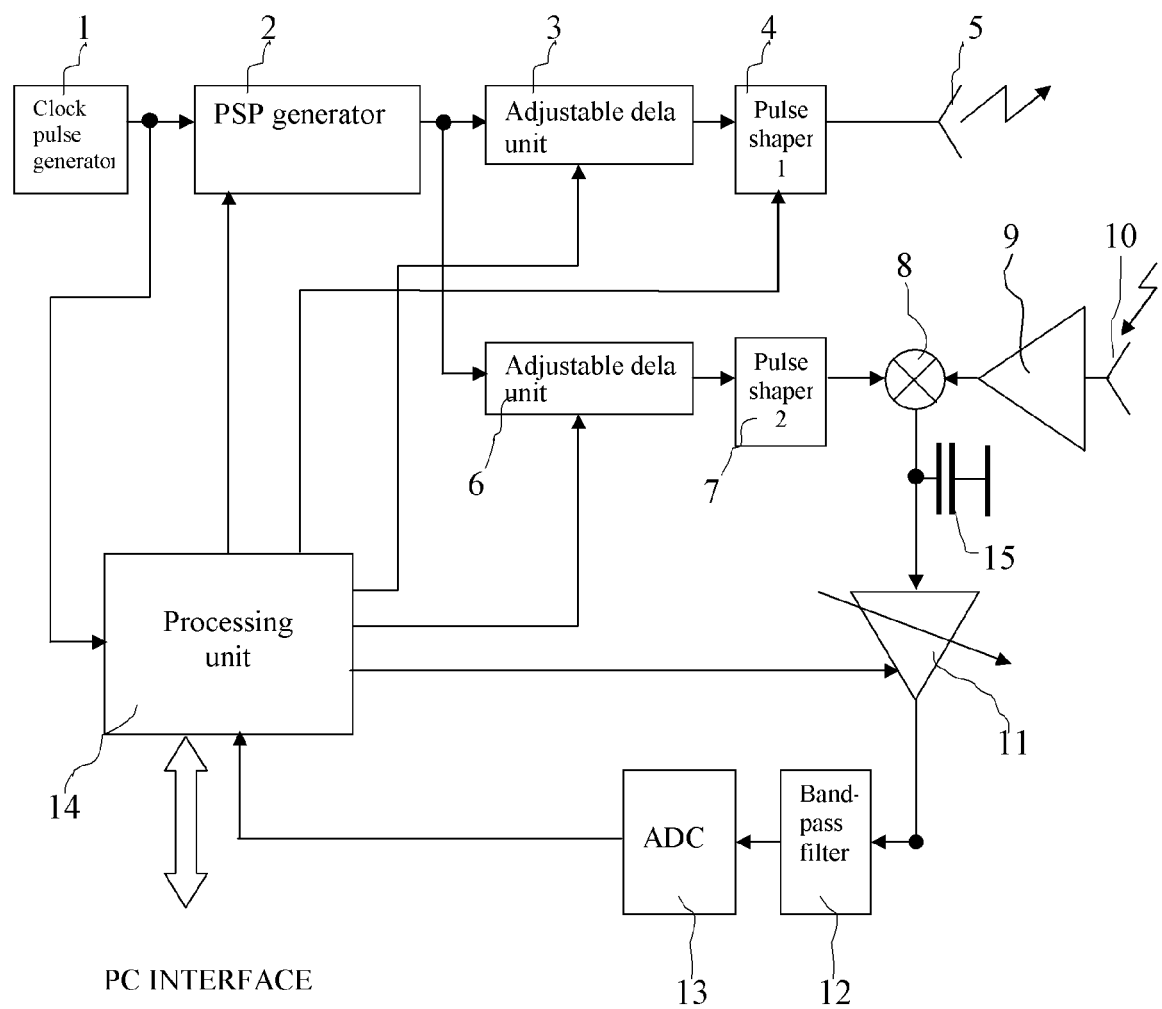
FIG. 1 shows the functional scheme of the inventive locator.

Since the inventive method is implemented in the locator operation, we shall first describe the functional elements included into its structural diagram (FIG. 1).

A locator for monitoring living beings comprises a clock pulse generator 1, a pseudorandom sequence pulse (PSP) generator 2, a first adjustable delay unit 3, a first ultra-wideband signal pulse shaper 4 made controllable, a transmitting antenna 5, which are connected in series. The locator has a second adjustable delay unit 6, a second ultra-wideband signal pulse shaper 7, a mixer 8, an amplifier 9, a receiving antenna 10, an adjustable amplifier 11, a band-pass filter 12, an analogue-to-digital converter 13, a processing unit 14 and a capacitor 15. The input of the second adjustable delay unit 6 is connected to the output of the pseudorandom sequence pulse generator 2, and its output is connected to the input of the second ultra-wideband signal pulse shaper 7. The output of the second shaper 7 is connected to the first input of the mixer 8. The receiving antenna 10 is connected to the input of the amplifier 9 which output is connected to the second input of the mixer 8.

The adjustable amplifier 11, the band-pass filter 12, the analogue-to-digital converter 13 are connected in series. the input of the adjustable amplifier 11 is connected to the output of the mixer 8.

One terminal of the capacitor 15 is connected to the output of the mixer 8, and the other terminal of the capacitor 15 is connected to the housing. The clock input of the processing unit 14 is connected to the output of the clock pulse generator 1, and its control input is connected to the output of the analogue-to-digital converter 13.

The processing unit 14 is made with five control outputs. The first control output of the processing unit 14 is connected to the control input of the first ultra-wideband signal pulse shaper 4, its second control output is connected to the control input of the first adjustable delay unit 3, its third control output is connected to the control input of the second adjustable delay unit 6, and its fourth control output is connected to the control input of the adjustable amplifier 11. The fifth control output of the processing unit 14 is connected to the control input of the pseudorandom sequence pulse generator 2. The processing unit 14 is made with the possibility of separating a modulated component corresponding to a living being pulse or breath rate. The processing unit 14 is made so as to ensure shaping of ultra-wideband signal pulse packets with the possibility of regularly switching on/off according to the control input of the first ultra-wideband signal pulse shaper 4.

The processing unit 14 ensures changes in a delay according to the control input of the second adjustable delay unit 6 for the purpose of fixing a check point position in the middle range of the voltage amplitude characteristic for an ultra-wideband signal received by the receiving antenna 10, memorizing that check point position and changing a delay according to the control input of the first adjustable delay unit 3 when that check point position changes. The processing unit 14 ensures changing a delay according to the control input of the second adjustable delay unit 6 for the purpose of ranging a living being. The processing unit 14 is made so as to ensure changing a gain coefficient of the adjustable amplifier 11 for the purpose of compensating for attenuation of an ultra-wideband signal received by the receiving antenna when a distance to a living being increases.

Figure 2:
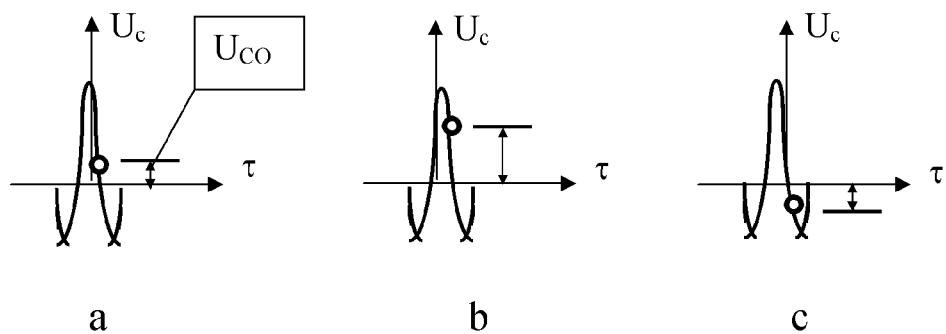
FIG. 2 depicts: a) selection of a check point on an amplitude characteristic of a correlated signal for the purpose of realizing stabilization of a signal time position, b) and c) possible drifts of the check point due destabilizing factors, e.g., trembling of a locator or a change in temperature.

The method for stabilizing time position of an ultra-wideband signal comprises shaping ultra-wideband signal pulses by the first shaper 4 according to a reference signal from the PSP generator 2 (FIG. 1). A shaped ultra-wideband (UWB) signal is emitted to space by the transmitting antenna 5. The UWB signal is received by the receiving antenna 10. The received UWB signal is processed by its mixing (multiplying) in the mixer 8 with a reference ultra-wideband signal shaped by the second UWB signal pulse shaper in order to obtain a correlated signal. When processing the received UWB signal, the reference UWB signal shaped by the second UWB signal pulse shaper 7 is delayed by the time during which an initial position of an Uco check point (FIG. 2a) is set at the middle range of the correlated signal at the capacitor 15 after the mixer 8 (the middle range is understood as a section located in the middle of the correlated signal amplitude characteristic, namely, between the maximum and the minimum voltages of the correlated signal or at the point of the correlated signal, which is characterized by maximum steepness). The position of that Uco check point is regularly monitored between receptions of next UWB signals reflected by an object; the object is ranged at such receptions. When receiving next UWB signals reflected from an object, and if the position of the Uco check point shifts from the initial position (FIG. 2 b, c), a delay in emitting to space an UWB signal shaped by the first shaper 4 is changed by the first adjustable delay unit 2, in the result of which the position of the Uco check point is reset (FIG. 2 a).

The initial position of the Uco check point may be set by various methods. For example, it can be set before receiving next ultra-wideband signals reflected from an object by emitting by the receiving antenna 5 an UWB signal, as shaped by the first pulse shaper 4, directly to the space area where the receiving antenna 10 receives next ultra-wideband signals reflected from the object. That is, a sequence of direct passing from the transmitting antenna 5 to the receiving antenna 10 is used. In such a case, during stabilization the value of a correlated signal at a Uco check point in the range of an amplitude characteristic, e.g., having a greater steepness, is memorized. In the future such value is regularly checked and, depending on an error value, the value of a delay for the first adjustable delay unit 2 is changed. The said stabilization is carried out automatically in time intervals set by the developer, thus eliminating temperature drifts of a delay in an ultra-wideband signal emitted by the transmitting antenna 5 to space.

As a variant, a reference signal for stabilization may be selected in the scanning mode by indicating, with the use of a marker, a stabilized check point for a signal. The signal value at a selected Uco check point is regularly read (e.g., once during the period of scanning the distance). Furthermore, an initial position of the Uco check point may be set when receiving an ultra-wideband signal reflected from an immovable (nonliving) object. In such a case the inventive method enables to eliminate small movements of the locator, which are caused, e.g., by trembling hands of the locator operator. The said stabilization may be also carried out automatically in time intervals between receiving UWB signals from a living being.

Stabilization is especially important in work with UWB signals having pulses of small duration. For pulses with the duration of 100 picoseconds an error in stabilization of a time delay should be not less than 1 picosecond.

It is expedient to select, as the position of an Uco check point, such a check point position on the amplitude characteristic of a Uc voltage of a correlated signal where the said characteristic has the maximum steepness (FIG. 2a). A value of the Uco reference voltage is measured, and, if current Uc values for next ultra-wideband signals reflected from an object become different from the Uco value of the reference voltage (FIG. 2b, 2c), a delay of the first adjustable delay unit 3 for emitting a shaped ultra-wideband signal to space is changed with due account to the Uc voltage current value, at negative steepness of a signal at the check point and Uc>Uco a delay of the first adjustable delay unit 3 being decreased and at Uc<Uco a delay being increased. The law of changing delay may be reversed if the signal steepness at the check point is positive. A decrease or increase in a delay is determined by the steepness sign at a check point selected for reading of the reference voltage. Thus, a difference between the current value of Uc voltage and the reference Uco voltage is monitored by the processing unit 14 and used for controlling the delay time of the first adjustable delay unit 3.

Moreover, the inventive method enables to set the stabilization parameter e selected according to the value by which the Uco voltage exceeds the noise level Um at the check point. For example, a suitable value would be triple mean-square noise value.

Of fundamental importance is the fact that the inventive method enables to work with ultra-wideband signals having different forms and with absolutely different sequences of UWB pulses. In particular, as discussed below, a pulse packet may be used as an ultra-wideband signal, each pulse in the packet having the form of one harmonic vibration period.

Also, a pulse sequence with equal time intervals between pulses as well as a pseudorandom sequence pulse sequence may be used as an ultra-wideband signal.

The locator (FIG. 1) works as follows.

Figure 3:
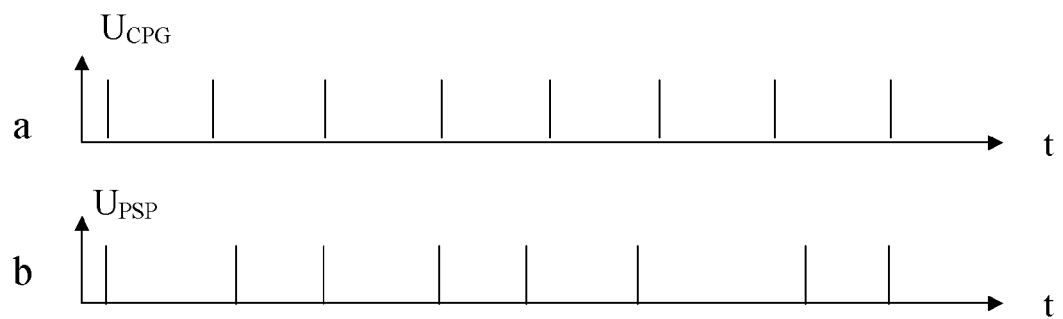
FIG. 3 shows time diagrams of a) clock pulses and b) pseudorandom sequence pulses (PSP)

The clock pulse generator generates a periodic clock pulse sequence (FIG. 3a) actuating the PSP pulse generator 2. A time pseudorandom sequence with the $T_{PSP}$ period is shaped in the PSP pulse generator 2 from pulses emitted by the generator 1 (FIG. 3b), which further comes to the first and the second adjustable delay units 3 and 6, respectively. The PSP pulse generator 2 shapes pulses which sequence interval changes according to a certain set law. Signals from the output of the first adjustable delay unit 3 actuate the first ultra-wideband signal (probing signal) shaper 4 connected to the transmitting antenna 5. Signals from the output of the second adjustable delay unit 6 come to the second UWB pulse shaper 7 shaping a heterodyne signal for the mixer 8.

Figure 4:
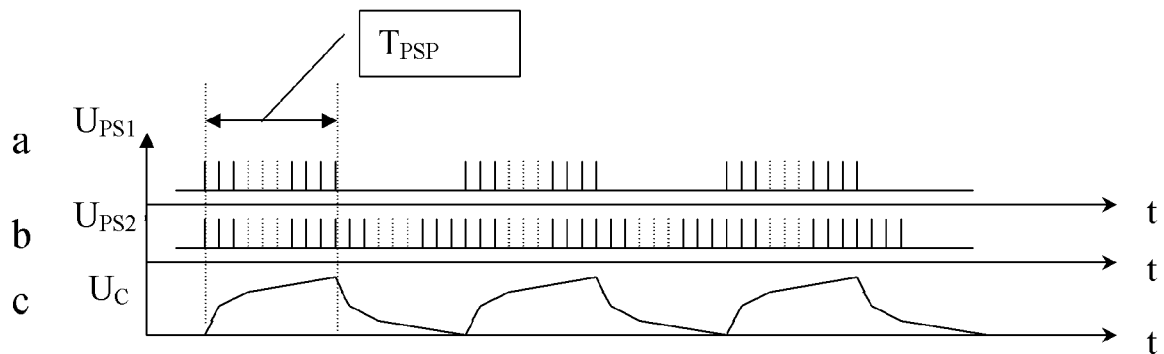
FIG. 4 shows time diagrams of a) a PSP pulse packet at the output of the first ultra-wideband signal pulse shaper, b) a PSP pulse packet at the output of the second ultra-wideband signal pulse shaper, c) form of a signal at the capacitor (integrator) when delays of the first and the second ultra-wideband signal pulse shapers coincide.

In order to ensure the possibility of forming a receiver intermediate frequency the first shaper 4 works in the mode of shaping pulse packets. During one period of a PSP sequence the first shaper 4 is on and during the following period it is off (FIG. 4a)—a $U_{PS1}$ signal. In order to provide this mode the first shaper 4 is connected by its control input (interlock input) to the first control output of the processing unit 14. Signals from the second UWB pulse shaper 7 come to the mixer 8 without interruptions (FIG. 4b)—a $U_{PS2}$ signal.

A pulse sequence reflected from an object is received by the receiving antenna 10, comes to the amplifier 9 and then to the mixer 8. In the mixer 8 the signals reflected from the object and the heterodyne signal from the output of the second UWB signal shaper are multiplied together. The resultant signal comes from the output of the mixer 8 to the integrator made on the basis of the capacitor 15. If the delay of signals reflected from a remote object and that of the heterodyne signal coincide, a correlated signal in the form of a periodic wave sequence is formed at the capacitor 15, the amplitude of the said waves being proportional to the amplitude of the reflected signals and their period corresponding to the double period of repetition of the PSP sequence (FIG. 4c)—a Uc signal.

After being integrated by the capacitor 15, the pulses are amplified in the adjustable amplifier 11 having a variable gain coefficient. The gain coefficient of the adjustable amplifier 11 is set according to the fourth control output of the processing unit 14, which is connected to the control input of the adjustable amplifier 11, thus enabling to create different amplification in the beginning and in the end of scanning and compensating for signal attenuation caused due to increased distances to reflecting objects. During the time corresponding to the PSP duration signals are accumulated at the output of the mixer 8 at the capacitor 15. The band-pass filter 12, which selects the first intermediate frequency, is connected to the output of the adjustable amplifier 11. The first intermediate frequency is defined by the duration of a pulse sequence coming to the first UWB signal pulse shaper 4. This signal is converted from analogue to digital in the analogue-to-digital converter 13 and then comes to the control input (digital data input) of the processing unit 14 converting the received signal to zero intermediate frequency and selecting the amplitude of the reflected signals for the purpose of analyzing the components corresponding to the breath and pulse of a living being.

Figure 5:
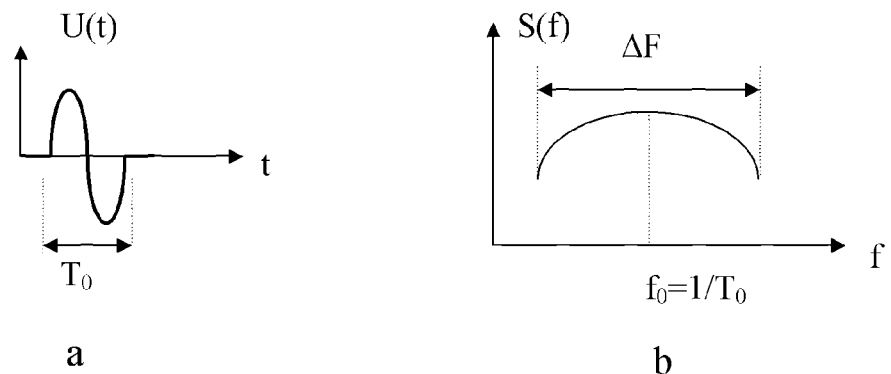
FIG. 5 shows a) form of a transmitted ultra-wideband signal for one pulse, b) spectral density of am ultra-wideband signal for one pulse.

The first UWB signal pulse shaper 4 shapes a probing signal from actuating pulses sent by the PSP generator 2. As one pulse of a probing signal in the locator it is expedient to use a pulse in the form of one harmonic vibration period (FIG. 5a). The use of such a signal form enables to efficiently emit it by the transmitting antenna 15. The central frequency $f_0$ of the pulse spectrum and the effective bandwidth ΔF occupied by this signal are equal to $1/T_0$ (FIG. 5b). Compared to a pulse signal in the form of a Gaussian pulse, this signal comprises a significantly lower level of spectral components at low frequencies and, therefore, may have a better match with the transmitting antenna 5 and the receiving antenna 10 during emission and reception, respectively.

Figure 6:
FIG. 6 shows a pseudorandom sequence of an UWB signal of a pulse packet.

Due to a PSP actuating pulse sequence coming from the generator 2 to the first shaper 4, the form of signals emitted by the transmitting antenna 5 for a pulse in the form of one harmonic vibration period corresponds to that shows on FIG. 6. The form of pulses at the output of the second shaper 7 coincides in its form to that of pulses at the output of the first shaper 4.

In order to determine positions of reflecting living beings in respect of distances to them, ranging scanning is carried out. In this mode the value of a delay in the second adjustable delay unit 6 is changed successively for each distance coordinate (FIG. 1). Voltage is accumulated at the capacitor 15 over the time equal to the PSP duration. This voltage is amplified by the adjustable amplifier 11, read in the digital form by the analogue-to-digital converter (ADC) 13 and stored in the memory of the processing unit 14. Then the value of a delay in the second adjustable delay unit 6 is changed, and a new voltage value is read. If there is a reflecting living being on the distance coordinate L, then, when a sequence is delayed at the output of the second adjustable delay unit 6 by the time 2L/c, where c stands for velocity of light, a voltage proportional to the amplitude of the reflecting living being is separated at the capacitor 15. A shift of a received sequence Uo relative to the reference sequence $U_{PS2}$ coming to the mixer 8 from the second shaper 7 leads to a change in the voltage present at the capacitor 15 in accordance with the diagrams shown on FIG. 7a, 7b, 7c. The duration of a pulse Uc taken from the capacitor 15 is equal to the duration of a probing signal To when a signal delay in the second adjustable delay unit 6 is changed, and the signal form corresponds to the correlation function of the reflected signal and the heterodyne signal. If several reflecting living beings are present, response of each of them will be observed at a delay T equal to the signal propagation time to a living being and back. When determining parameters of living beings a delay π of the heterodyne signal $U_{PS2}$ is fixed at a point ensuring the maximum of the received signal, and the processing unit 14 determines the breath and heartbeat parameters according to a change in the amplitude.

The breath and heartbeat parameters are measured by the processing unit 14 as follows. After performing the operations on stabilizing a delay of an emitted ultra-wideband signal with the use of the first adjustable delay unit 3 and successive change of a signal delay in the second adjustable delay unit 6 from some initial value to a final value by a preset step, which values are determined by a selected range of studied distance and a necessary discreetness for distance, N samples of voltages at the capacitor 15 are successively written into RAM. A microcontroller in the processing unit 14 enables to analyze and compute the signal parameters written into RAM (amplitude, dispersion, frequency). A definite distance corresponds to each value of delay in the second adjustable delay unit 6. At the same time, a signal reflected from a living human being is delay-modulated, and, therefore, its value at a given value of delay in the second adjustable delay unit 6 is changed. The modulation frequency for breath is 0.05-0.3 Hz, and for heartbeat 0.7-3 Hz. After writing a real reflected signal in a preset range according to delay ranges for each value of a delay in the second adjustable delay unit 6 into the memory of the processing unit 14 dispersion of written voltages is computed for N points. If living human beings are present, dispersion of a reflected signal at a delay (distance) corresponding to their location will exceed dispersion of reflected signals at other delays. The processing unit 14 selects for a delay in the second adjustable delay unit 6 such a value at which there is a maximum voltage dispersion or at which a dispersion value exceeds an additive noise dispersion level. Then the Uc voltage corresponding to reflection of a modulated signal carrying the life components of a human being is successively read and written into the memory of the processing unit 14. This voltage Uc is filtered at the digital filter, and the processing unit 14 measures its period of change. Depending on what is measured—either breath or heartbeat—parameters are written to the digital filter, which correspond to a filter with the bandwidth 0.7-3 Hz or 0.05-0.3 Hz. Frequency is measured after digital filtering. In the simplest case frequency is defined as a reciprocal to the signal voltage repetition period. Period is measured as a time interval after which a signal value begins repeating. Another algorithm for determining frequency is also possible, which consists in using the Fourier discrete transformation method for signal time realization received at a given value of a delay of the second adjustable delay unit 6 and selecting as frequency that of a spectral component having the maximum amplitude value.

Figure 8:
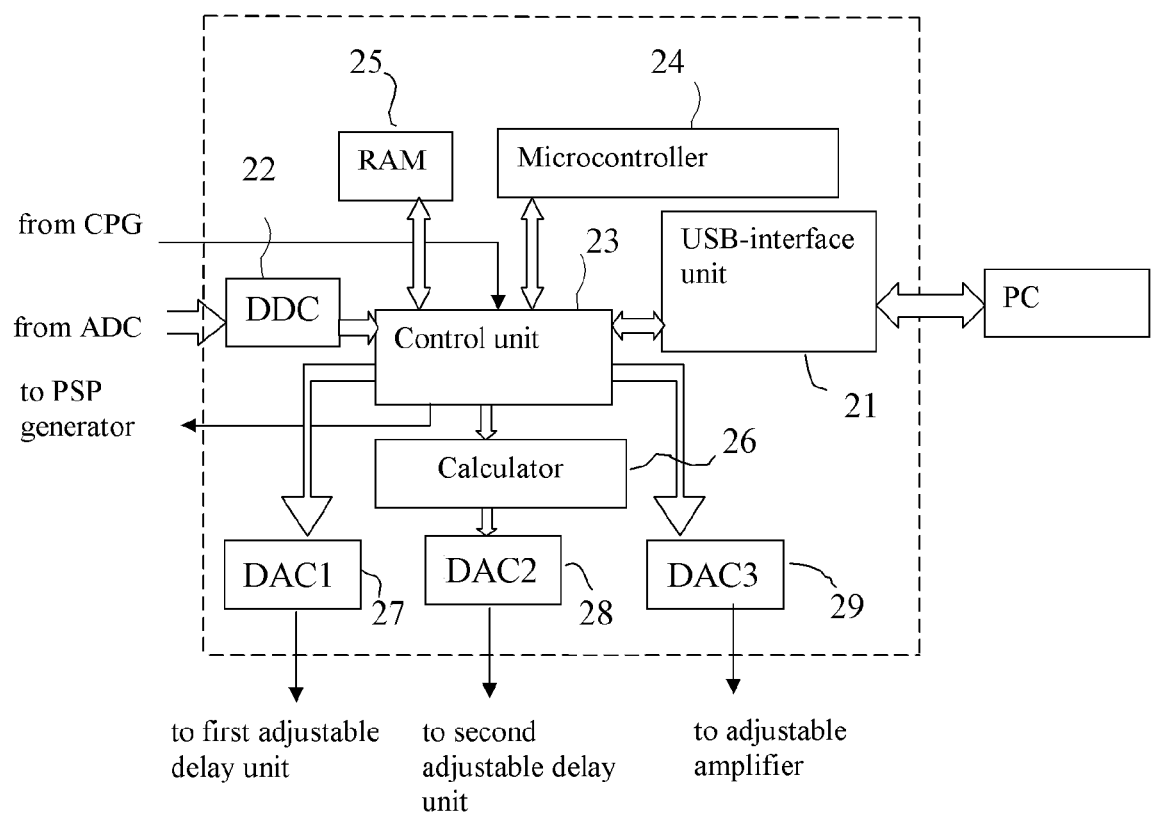
FIG. 8 shows the functional scheme of the processing unit.

The processing unit 14 (FIG. 8) also maintains communication with a personal computer (PC) through a USB-port for the purpose of obtaining instructions from the personal computer, sending information to the personal computer, updating the computer software used for control of the locator components and units (FIG. 1). Also, PC may measure the parameters of reflected signals (frequency and amplitude of reflected signals, etc.) and visualize them on its display.

The processing unit 14 comprises the following components (FIG. 8): a USB-interface unit 21 (may be made on a Cypress chip CY7C68001-56PVC), a digital filtering unit 22 (DDC) that may be made on an Analog Devices chip AD6620, a control unit 23, a microcontroller unit 24, a RAM device 25, for which a Samsung chip K6R4016V1D-TI08, a calculator 26 (the control unit and the calculator may be made on an ALTERA EPLD chip EP1K50QI208-2), digital-to-analogue converters DAC1-27, DAC2-28, DAC3-29 (an Analog Devices chip AD5542 may be used as DAC). The functional scheme of the calculator is shown on FIG. 9. The calculator comprises a value code register 30 for check point Uco voltage, a value code register 31 for check point Uc voltage, a subtractor 32, a comparator 33, an error code register 34, a code corrector 35, a code register 36 for the first adjustable delay unit.

The USB-interface unit 21 is intended for exchanging information with an external personal computer through a USB-port. The DDC unit 22 is intended for information processing. The processing includes frequency conversion and band-pass or low-frequency filtering, type and form of information processing is determined by instructions coming from a microcontroller or a personal computer. The control unit 23 is intended for controlling all the locator components according to control outputs of the processing unit 14 обработки. Also, it serves for obtaining data from the analogue-to-digital converter 13, loading it into the digital filtering unit 22, obtaining filtered data from the digital filtering unit 22, sending information to the USB-interface unit 21 for its further sending to a personal computer, loading data from a personal computer through the USB-interface unit 21, loading codes for shaping PSP signals according to the fifth control output of the unit 14, for actuating the first shaper 4 and the second shaper 7, for computing amplitude, dispersion and frequency parameters of reflected signals in accordance with the above-discussed algorithm.

The microcontroller unit 24 is intended for pre-start loading of firmware, testing the locator components and units, sending, if necessary, test results to an external personal computer, computing reflected signal parameters (amplitude, delay, frequency) and, if necessary, sending information to other devices, such as a line display, a loud speaker, etc.

The processing unit 14 (FIG. 8) works as follows. Data from the ADC 13 is written into the DDC 22, where frequency is digitally converted from the first intermediate frequency to the carrier with zero frequency, and the resultant signal is filtered in the low-frequency filter of the band-pass filter. Thus, either a breath rate or a heartbeat rate may be selected. An AD6620 chip comprises all the necessary technical means for conversion and digital filtering of signals. In the realization record mode in accordance with the algorithm (FIG. 10) the control unit writes instances of reflected signals into RAM 25. After actuating the auto stabilization mode the control unit 23 writes into the calculator 26 a code value received from the analogue-to-digital converter and corresponding to a signal value at the check point on realization (Uco value code register 30) according to which stabilization is carried out. A code value corresponding to delay half-scale is entered into the code register for the first adjustable delay unit 36. A value of the adjustment threshold s is entered into the error code register 34. The mode of successively taking signal realizations is actuated. A new signal value received from the analogue-to-digital converter is entered into the check point Uc value code register 31 for the same realization check point for which a Uco value was previously entered into the Uco value code register 30. A signal is entered into the Uco value code register only once at the time of actuating the stabilization mode, and it is not changed in the process of stabilization. A signal is entered into the Uc value code register 31 each time when a next signal realization is taken, subtraction of the Uc and Uco codes is made in the subtractor 32, and in the comparator 33 the subtraction module is compared with the threshold value s. Depending on the difference sign and the result of comparison between an error and the threshold value e in the comparator 33, a new code value, which is greater or lesser by 1, is entered into the code register for the first adjustable delay unit 36. This is carried out with the use of the code corrector 35. In the result of cyclical carrying-out of the algorithm (FIG. 11) the Uc code value will be approximated to the Uco value with an error not greater than the value of s, so the time position of a signal taken as the reference signal for stabilization will correspond to the time position at actuating the auto stabilization mode.

DAC1 27 and DAC2 28 are used for changing a delay value in the first adjustable delay unit 3 and the second adjustable delay unit 6. DAC3 29 is used for controlling the adjustable amplifier 11.

EPLD (erasable programmable logic devices) or FPGA (field programmable gate arrays) are used in the processing unit 14 for realization of the control unit 23 and the calculator 26. For their operation after turning on the power supply the microcontroller 24 loads the configuration file defining their internal structure. There are several loading methods described in recommendations of ALTERA, one of them uses a microcontroller (see Application Note 116). The configuration file defines the internal "content" of EPLD, its behavior and response to input signals. Therefore, after turning on the power supply the first configuration file is loaded into EPLD, which is required for enabling the EPLD circuits to test the device components and units (the LOADER mode). If the test is successful, the other configuration file is loaded that is intended for transferring EPLD into the device operation mode (RUN). The microcontroller stores these two configuration files for EPLD in its flash-memory.

After turning on the power the control over the unit is transferred to the microcontroller unit 24. The unit 24 comprises a microcontroller and a data memory. The microcontroller initializes the USB-interface chip 21, loading into it data from the data memory. Similarly, the configuration files for the EPLD circuits are loaded from the data memory (the LOADER mode of operation). The microcontroller conducts the system tests, actuates data collection from points, conducts tests of the ADC 13, DDC 22, etc. Test results may be sent through the USB interface to an external computer. If no errors are identified during the tests, the instruction to load the configuration files for the EPLD circuits for the operation mode 2 (RUN) is issued. At this point there are some variants possible, which depend on the version of the configuration file stored in the microcontroller memory and used while working with an external PC. If the external computer has a later version, it is first loaded from an external program to the microcontroller memory and then loaded to EPLD. After loading the EPLD configuration for the operation mode 2 the device enters into the main operation mode. The device control is transferred from the microcontroller unit 24 to the control unit 23, since the greater requirements relating to the processing rate and control cannot be met by the microcontroller unit 24, but are fulfilled by the logics of the control unit 23. The external program loads realization point codes, realization signal amplification codes and other parameters set by the user. The processing unit 14 collects this data and either sends it to the external computer or computes, processes and indicates the reflected signal parameters, e.g., a signal amplitude change rate.

Figure 9:
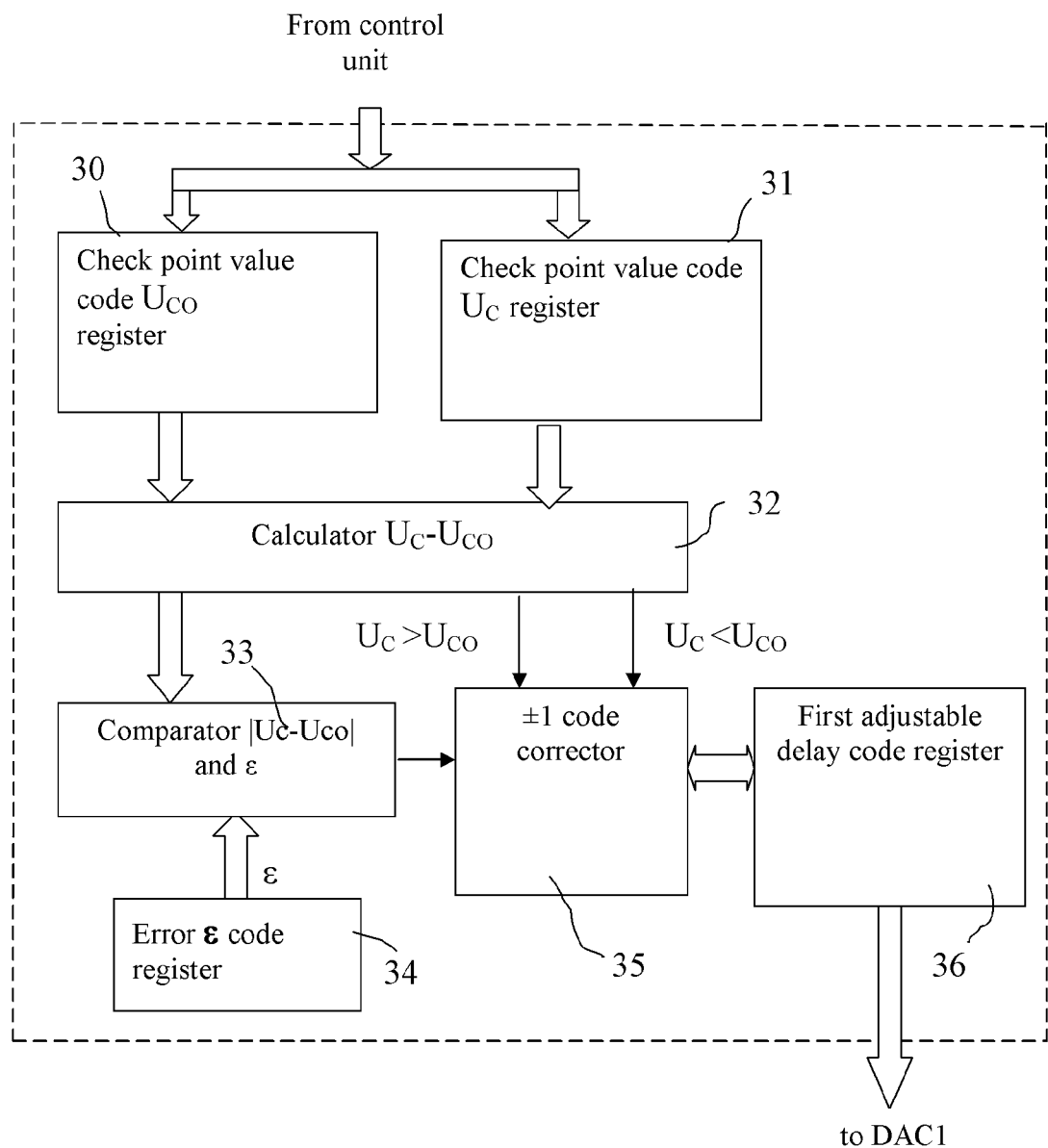
FIG. 9 shows the functional scheme of the calculator.
Figure 10:
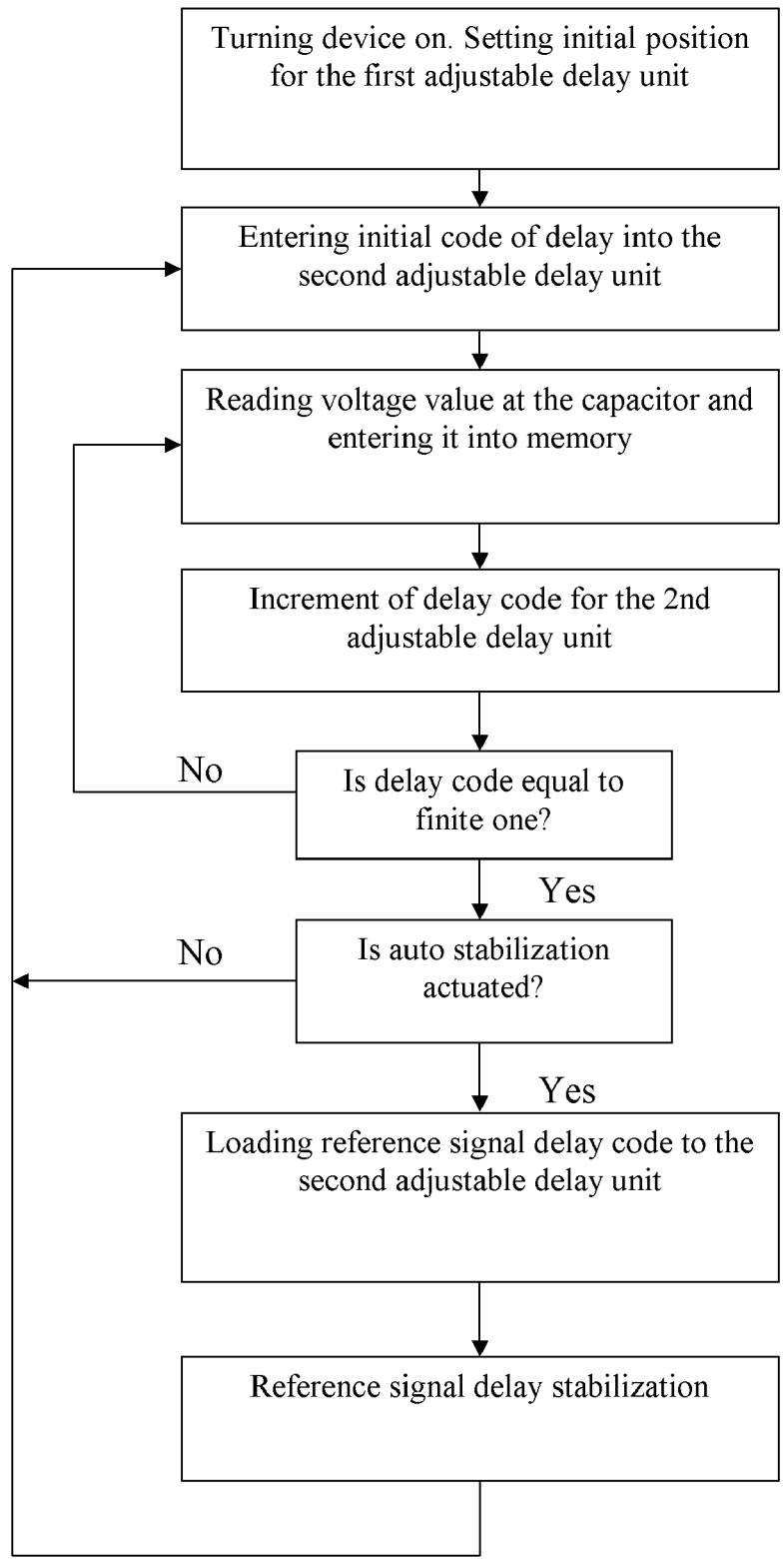
FIG. 10 shows an operation algorithm of the processing unit control circuit in the mode of scanning and stabilizing a reference signal delay.

The control unit 23 works in the scanning mode as follows (FIG. 10). After turning on the power the microcontroller unit 24 (FIG. 9) loads the initial value code for the first adjustable delay unit 3 (mean delay value) and starts performing operations on entering a reflected signal realization. For this the initial delay code is written into the second adjustable delay unit 6 (FIG. 1), which ensures reading a signal from a preset initial distance, the value of Uc voltage at the capacitor 15 is read and written into RAM 25, the delay code for the second adjustable delay unit 6 is incremented, and a voltage at the capacitor 15 is written once again. The said operations are repeated until all the delay (distance) range is covered. According to their results an array is formed in RAM 25, which represents realization of reflected signals in the set range of delays (distances).

Figure 11:
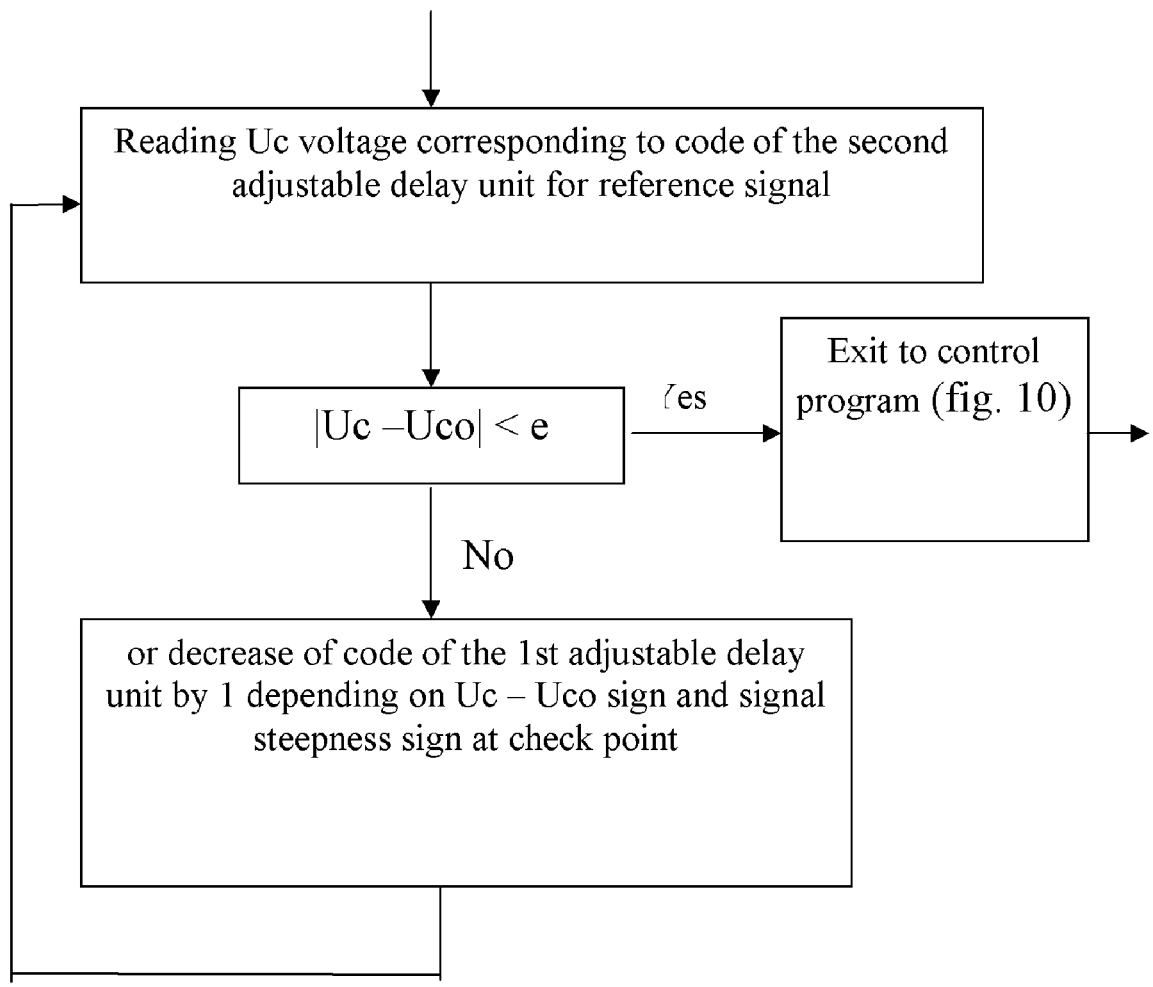
FIG. 11 shows an algorithm of stabilizing a reference signal delay.

In order to stabilize UWB signal time position (FIG. 2) the control unit 23 included into the processing unit 14 works as follows (FIG. 11). It calculates a difference between a current value of Uc voltage at the check point and the value memorized at actuating the program for stabilizing Uco. Depending on steepness at the check point and the sign of the said difference, a delay in the first adjustable delay unit 6 is either increased or decreased (FIG. 1). If the said difference is less than the threshold value e that is selected on the condition of excess over the noise level Un, |Uc−Uco|<e, then control program is executed for the purpose of distance scanning (FIG. 9). The operation on time position stabilization is carried out once in each cycle of taking a reflected signal realization. If the period of taking one sample on a delay is 1 microsecond, and the number of samples during realization is 1000, then the repetition time for the stabilization operation is 1 millisecond. For the time of app. 1 millisecond a delay in the check point may not significantly change, and the check point may not go beyond the limits of a monotonous section of the correlated signal amplitude characteristic, since such changes are caused by slow processes occurring due to mechanical movements and temperature changes. At the same time, the said operation ensures stable time position of an emitted signal relative to a selected reference signal during realization of a reflected signal. When duration of a probing signal is not more than 0.5 nanosecond, duration of a monotonous section is not more than 0.2 nanosecond. If an amplitude of a reference signal used for stabilization is 0.5 V and the noise level of a receiver is 0.5 mV, then an error in time stabilization, when the threshold e is equal to double value of noise voltage e=1 mV, would be ~200 picoseconds 1 mV/500 mV=0.4 picosecond. Even better stabilization accuracy may be achieved if a voltage value read at the check point is averaged. In such a case an error will be decreased as $\sqrt{M}$, where M stands for a number of averaged samples.

Thus, compared to the closest analogous solution, the inventive implementation of the locator (FIG. 1) ensures that:

Forming a first intermediate frequency at reception, which is ½ $T_{PSP}$. Forming a first intermediate frequency enables to amplify a signal at frequencies where the influence of flicker noises from semiconductor elements is small. The proposed scheme for forming actuating pulses in the form of a periodic sequence of coded pulse packets with an interval of interruption in emission (FIG. 4a) enables to eliminate synchronous low-frequency interferences at the mixer 8, the transmitting antenna 5 and the receiving antenna 10. In such a case main amplification is at an intermediate frequency, being subjected to smaller effect of flicker noises. The value measured in such a case is an alternating voltage amplitude between voltage at the output of the mixer 8, which is taken when emitting a probing signal, and voltage at the output of the mixer 8, which is taken when the first shaper 4 is not actuated.

Emission of pulses distributed over time according to a pseudorandom order enables to reduce spectral density of pulses at discrete frequency components determined by the repetition period of the generator 1 (CPG) and, consequently, reduce the influence on the other locator units. In contrast to an analogous solution, the present scheme for shaping actuating pulses with the use of the PSP generator 2 enables to shape pseudorandom sequences of probing pulses within the limits from −T/2 to T/2, where T stands for a period of pulse sequence issued by the CPG generator 1. For example, the use of orthogonal M-sequences as PSPs has optimal correlation properties in respect of signal/noise relation at correlation reception. Knowledge of the PSP law and frequency is enough for realizing an autonomous channel for receiving probing signals, which is important for realizing multi-channel schemes. At the same time, the pseudorandom law of sequencing makes an emitted probing signal closer to a noise signal, thus eliminating synchronous interferences, which act on other locator units, at frequencies equal to a repetition period of a probing signal.

Figure 7:
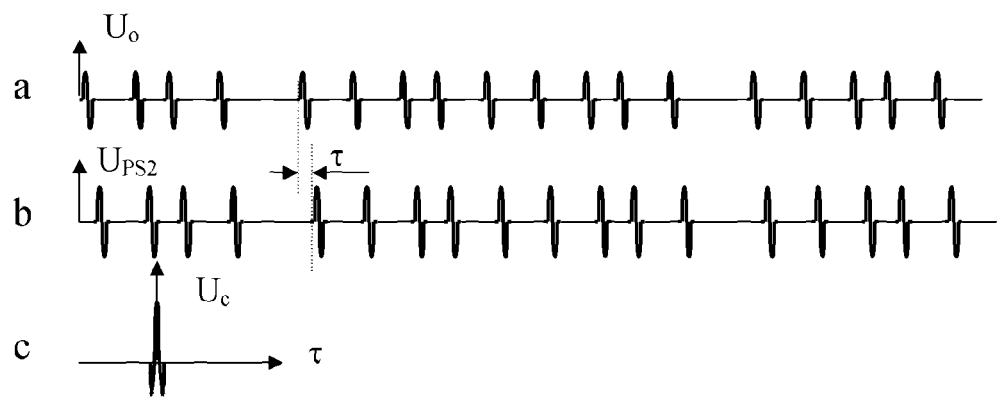
FIG. 7 shows a) a received UWB signal, b) a heterodyne signal at the output of the second ultra-wideband signal pulse shaper, c) a voltage amplitude at the correlator (mixer and capacitor) depending on mutual time shift of signals T.

The most important thing is that the inventive method and device enable to stabilize time positions of reflected signals relative to any preset time signal received by the receiving antenna 10. Stabilization 15 is required, since with a change in temperature or a locator position a delay of a signal received from a useful object is changed also. At small mutual shifts of time sequences of a received signal $U_0(t)$ and a heterodyne signal $U_{PS2}(t)$ an amplitude of a registered signal rapidly changes (FIG. 7). In order to correctly read a signal from a preset distance long-term stability of an UWB signal time position is required.

INDUSTRIAL APPLICABILITY

The inventive method for stabilizing time position of an ultra-wideband signal and the inventive locator for monitoring living beings are industrially applicable for the purposes of searching and determining coordinates of living beings by search and rescue services; and the inventive method may be applied in other technical applications using pulse signals having duration of several nanoseconds or less.

What is claimed is:

1. A method for stabilizing time position of an ultra-wideband signal, comprising:
    shaping an ultra-wideband signal according to a first reference ultra-wideband signal thus forming a shaped ultra-wideband signal,
    emitting the shaped ultra-wideband signal to space,
    receiving a received ultra-wideband signal,
    processing the received ultra-wideband signal by mixing it with a second reference ultra-wideband signal thus forming a correlated ultra-wideband signal, wherein,
        while processing the received ultra-wideband signal, said second reference ultra-wideband signal being delayed by a time during which an initial position of a check point in a middle range between maximum and minimum voltages of the correlated ultra-wideband signal being set,
        regularly monitoring a position of said check point, and when the position of said check point shifts from the initial position, a delay in emitting the shaped ultra-wideband signal to space is changed for resetting the position of said check point to the initial position.

2. The method according to claim 1, characterized in that the initial position of the check point is set before receiving next received ultra-wideband signals reflected from an object by emitting the shaped ultra-wideband signal directly to an area where the next received ultra-wideband signals reflected from the object are received.

3. The method according to claim 1, characterized in that the initial position of the check point is set when the reflected ultra-wideband signal reflected from an immovable object is received.

4. The method according to claim 1, characterized in that a pulse packet is used as the ultra-wideband signal, wherein the form of each pulse corresponds to one period of a harmonic vibration.

5. The method according to claim 4, characterized in that the pulse packet of pseudo-random sequence is used as the ultra-wideband signal.

6. A method for stabilizing time position of an ultra-wideband signal, comprising:
    shaping an ultra-wideband signal according to a first reference ultra-wideband signal thus forming a shaped ultra-wideband signal,
    emitting the shaped ultra-wideband signal to space,
    receiving a received ultra-wideband signal,
    processing the received ultra-wideband signal by mixing it with a second reference ultra-wideband signal thus forming a correlated ultra-wideband signal, wherein,
        while processing the received ultra-wideband signal, said second reference ultra-wideband signal being delayed by a time during which an initial position of a check point in a middle range between maximum and minimum voltages of the correlated ultra-wideband signal being set,
        regularly monitoring a position of said check point, and when the position of said check point shifts from the initial position, a delay in emitting the shaped ultra-wideband signal to space is changed for resetting the position of said check point to the initial position
        characterized in that a position of the check point in the range of the correlated ultra-wideband signal having the maximum steepness is taken as the position of the check point,
    a value of reference correlated voltage Uco is measured in the check point, and
    when a current value of correlated voltage Uc differs from the value of reference correlated voltage Uco, a delay in emitting to space of a formed ultra-wideband signal is changed so as to take into account the current value of correlated voltage Uc, wherein
        for negative steepness of the correlated ultra-wideband signal at the check point and Uc>Uco, the delay being decreased,
        for negative steepness of the correlated ultra-wideband signal at the check point and Uc< Uco, the delay is increased, for positive steepness of the correlated ultra-wideband signal at the check point and Uc>Uco, the delay is increased, for positive steepness of the correlated ultra-wideband signal at the check point and Uc< Uco, the delay is decreased.

7. The method according to claim 6, characterized in that the stabilization parameter e is set, which is selected on the condition that the Uco voltage exceeds a noise level Un at the said check point.

8. A locator for monitoring living beings, comprising connected in series a clock pulse generator, a pseudorandom sequence pulse generator, a first adjustable delay unit, a first ultra-wideband signal pulse shaper made controllable, and a transmitting antenna, further comprising a second adjustable delay unit, a second ultra-wideband signal pulse shaper, a mixer, an amplifier, and a receiving antenna, wherein an input of said second adjustable delay unit being connected to an output of said pseudorandom sequence pulse generator, an output of said second adjustable delay unit being connected to an input of said second ultra-wideband signal pulse shaper, the output of said second ultra-wideband signal pulse shaper being connected to a first input of said mixer, said receiving antenna being connected to an input of the said amplifier, and an output of said amplifier being connected to a second input of said mixer, further comprising connected in series an adjustable amplifier, a band-pass filter, and an analogue-to-digital converter, wherein an input of said adjustable amplifier being connected to an output of said mixer, further comprising a processing unit and a capacitor, wherein one output of said capacitor being connected to the output of said mixer and the other output of said capacitor being connected to a housing, a clock input of said processing unit being connected to an output of said clock pulse generator and the control input of said processing unit being connected to an output of said analogue-to-digital converter, the processing unit is made with five control outputs, wherein its first control output is connected to a control input of the first ultra-wideband signal pulse shaper, its second control output is connected to a control input of the first adjustable delay unit, its third control output is connected to a control input of the second adjustable delay unit, its fourth control output is connected to a control input of the adjustable amplifier, and its fifth control output is connected to a control input of the pseudorandom sequence pulse generator, wherein the processing unit is made with the possibility of selecting a modulated component corresponding to the pulse or breath rate of a living being, said processing unit is made with the possibility to provide shaping of ultra-wideband signal pulse packets with the possibility of regularly switching on/off, according to the control input of the first ultra-wideband signal pulse generator, said processing unit is made with the possibility to provide changing a delay according to the control input of the second adjustable delay unit for the purpose of fixing a check point position at the middle range between the maximum and minimum voltages of a correlated signal at the capacitor, said processing unit is made with the possibility of memorizing the check point position and changing a delay according to the control input of the first adjustable delay unit when the check point position is changed, said processing unit is made with the possibility to provide changing the delay according to the control input of the second adjustable delay unit for the purpose of ranging a living being, and said processing unit is made with the possibility to provide changing a gain coefficient of the adjustable amplifier for the purpose of compensating for attenuation of an ultra-wideband signal received by the receiving antenna if a distance to the living being is increased.

* * * * *